United States Patent [19]

Reid et al.

[11] Patent Number: 5,739,289
[45] Date of Patent: Apr. 14, 1998

[54] MONOCLONAL ANTIBODY TO HUMAN CELL ADHESION MOLECULE

[75] Inventors: Robert Alan Reid, Durham; John Jacob Hemperly, Apex, both of N.C.

[73] Assignee: Becton, Dickinson and Company, Franklin Lakes, N.J.

[21] Appl. No.: 714,901

[22] Filed: Sep. 17, 1996

Related U.S. Application Data

[62] Division of Ser. No. 408,093, Mar. 21, 1995, Pat. No. 5,688,916, which is a division of Ser. No. 40,741, Mar. 26, 1993.

[51] Int. Cl.$^6$ ..................................................... C07K 16/28
[52] U.S. Cl. .................. 530/388.1; 435/69.1; 435/70.2; 530/387.1; 530/350; 530/300; 424/143.1; 935/89

[58] Field of Search .................. 435/69.1, 70.2; 536/23.1, 23.5; 935/89; 530/350, 300, 387.1, 388.1; 424/143.1

[56] References Cited

PUBLICATIONS

Berglund et al. (1991) Eur. J. Biochem. 197:549–554.
Ranscht et al. (1984) J. Cell Biol. 95:1803–1813.
Moss et al. (1989) Development 9:85–94.

*Primary Examiner*—Stephen Walsh
*Assistant Examiner*—Kenneth A. Sorensen
*Attorney, Agent, or Firm*—Donna R. Fugit

[57] ABSTRACT

A human brain glycoprotein homologous to the mouse F3 and the chicken contactin/F11 adhesion molecules, nucleic acid sequences encoding the human brain glycoprotein and antibodies directed against the human brain glycoprotein.

2 Claims, No Drawings

MONOCLONAL ANTIBODY TO HUMAN CELL ADHESION MOLECULE

This is a division of application Ser. No. 08/408,093, filed Mar. 21, 1995 now U.S. Pat. No. 5,688,916, which is a division of application Ser. No. 08/040,741, filed Mar. 26, 1993.

FIELD OF THE INVENTION

The present invention relates to cell adhesion molecules and nucleic acid sequences which code for cell adhesion molecules. In particular, the invention pertains to human cell adhesion molecules and nucleic acid sequences which code therefor.

BACKGROUND OF THE INVENTION

Adhesion between cells plays an essential role in development and maintenance of tissue form and function. Intercellular adhesion is mediated by a class of adhesive cell surface proteins commonly referred to as "cell adhesion molecules" or "CAMs". These proteins have been identified and characterized in a phylogenetically diverse range of organisms and have been found in many cases to be highly conserved in structure. Certain cell surface CAMs are members of a superfamily of glycoproteins which are structurally related to immunoglobulins, i.e., their structure contains a number of extracelluar immunoglobulin-like and fibronectin Type III-like domains.

The immunoglobulin superfamily of CAMs includes the neural cell adhesion molecule (N-CAM), the L1 antigen, Ng-CAM, TAG-1, and others. These CAMs are believed to mediate homophilic binding between cells and have also recently been recognized as participants in heterophilic interactions with other cell surface molecules, extracellular matrix proteins and proteoglycans. Many are also believed to be involved in transmission of signals to the interior of the cell which modulate cell morphology, cell metabolism and cell adhesion. The means by which these molecules transmit signals to the interior of the cell is unclear.

The F11 antigen (F11) is a chicken neural cell surface-associated glycoprotein which is believed to be involved in neurite-neurite interactions. The cDNA sequence of F11 has been determined and it codes for a 1010 amino acid protein (Brümmendorf et al. (1989) Neuron 2: 1351–1361). The F11 molecule comprises six domains related to the immunoglobulin domain type C and four domains similar to the fibronectin Type III repeat. These structures are also present in L1 and N-CAM. The cDNA sequence of F11 was found to be almost identical to the cDNA sequence of the chicken neural glycoprotein contactin (Ranscht, et al. (1988) J. Cell Biol. 107: 1561–1573; Zisch, et al. (1992) J. Cell Biol. 119: 203–213) and it is now believed that the molecules are the same (contactin/F11). However, prior to Applicants' invention, the identity was not clear. A mouse neural cell surface protein, F3, has been identified and is the homologue of the chicken neuronal cell adhesion protein contactin/F11. The cDNA which codes for F3 has been cloned and sequenced, revealing an open reading frame encoding a 1020 amino acid protein having the characteristics of the immunoglobulin superfamily (G. Gennarini, et al. 1989. J. Cell Biol. 109: 775–788).

The present invention relates to CAMs involved in human neural cell adhesion. Specifically, the present invention provides the purification and characterization of the human counterpart of the mouse F3 and chicken contactin/F11 proteins, the preparation of monoclonal and polyclonal antibodies to the human contactin and nucleic acid sequences encoding the human contactin. E. Berglund, et al. (1987. J. Neurochem. 48: 809–815) have used monoclonal antibodies to characterize glycoproteins in human brain and have reported isolation and characterization of a molecule identified as Gp135 (E. Berglund, et al. 1991. Eur. J. Biochem. 197: 549–554; E. Berglund, et al. 1991. Brain Res. 549: 292–296). These authors sequenced the amino terminus of the protein and an internal peptide. On the basis of these sequences they identified a similarity to chicken contactin/F11 and mouse F3, however, the reported amino acid sequence of Gp135 is different from that of the human contactin molecule described herein. It was therefore also unclear prior to Applicants' invention whether or not human Gp135 was the direct homolog of F3, contactin/F11. E. Berglund and B. Ranscht later reported the isolation and partial characterization of cDNA clones encoding Gp135 (1992. Soc. Neurosci. Abst. 18: 1325, Abst. #560.5).

SUMMARY OF THE INVENTION

Using monoclonal antibodies, a human brain glycoprotein (human contactin) homologous to the mouse F3 and the chicken contactin/F11 adhesion molecules has been isolated and characterized. A complete coding sequence of the human contactin gene has been determined by sequencing of human neuroblastoma cDNA clones. The gene could potentially encode other, alternatively spliced complete coding regions as well. At the nucleotide level, the human cDNA is 86% homologous to the mouse F3 cDNA. The deduced amino acid sequences are 95% homologous and predict several common structural features, including six immunoglobulin-like and four fibronectin Type III-like domains, as well as multiple sites for Asn-linked glycosylation. The mouse, chicken and human glycoproteins all contain carboxy-terminal hydrophobic segments which may be important for linking the proteins to the cell surface via a phosphatidylinositol anchor.

The human contactin glycoprotein is approximately 135 kD molecular weight and may be purified by immunoaffinity methods using monoclonal antibodies. Partial sequencing of an internal peptide yielded an amino acid sequence identical to that predicted from the cDNA. The cDNA has been expressed in recombinant host microorganisms and the gene product has been shown to be immunoreactive with polyclonal antisera raised against the monoclonal antibody-purified human contactin antigen. Northern blot analyses of the RNAs of various human tissues demonstrated a single major approximately 6.5 kb human contactin transcript in adult brain. Multiple transcripts (6.8 kb, a 6.0 kb doublet and 4.2 kb) are expressed in retinoblastoma and neuroblastoma cell lines. A low level expression of approximately 6.8 and 6.0 kb transcripts, similar to those observed in transformed cell lines, was also detected in human lung and pancreas. Very weak 6.8 and 6.0 kb bands were seen in kidney and skeletal muscle.

DESCRIPTION OF THE DRAWINGS

FIG. 1 illustrates the relationships of the mouse F3 probes used to clone the human contactin cDNA, the cDNAs carried in the NX-7 and NXII-7 clones and the human contactin coding sequence.

DETAILED DESCRIPTION OF THE INVENTION

The human contactin cell adhesion protein of the invention may be isolated from any human neural tissue in which it is expressed. The preferred source is human brain tissue. While conventional chemical and biochemical methods for isolation may be employed, the human contactin cell adhesion protein is most preferably isolated by immunoaffinity methods using antibodies which recognize and bind to it. Immunoaffinity methods for isolating antigens are well known in the art and may be employed to isolate the human contactin of the is present invention using the appropriate monoclonal or polyclonal antibody which recognizes the human contactin molecule. Monoclonal antibodies such as the CF3 antibody described by E. Berglund, et al., supra, or the Neuro-1 antibody described below are preferred, the Neuro-1 antibody being most preferred for isolation of the human contactin protein.

Monoclonal antibodies which recognize the human contactin protein of the invention may be prepared using the methods of Kohler and Milstein ((1975) Nature 256: 495) as is known in the art. The preferred antigen for immunization is a preparation of adult human brain membranes and the most preferred antigen is a synaptosomal fraction of these membranes which is enriched for cell surface glycoproteins. Mice may be immunized with the antigen preparation, the spleen cells fused and the resulting hybridomas screened against the original immunogen to select hybridomas.

Using these methods, a hybridoma which produces the monoclonal antibody herein designated Neuro-1 was identified. A crude synaptosomal membrane fraction was prepared from adult human brain tissue (Carlin, R. K., et al. (1980) J. Cell. Biol. 86: 831–843)). Membrane glycoproteins were extracted with TERGITOL Type NP-40 (polyglycol ether surfactant, Union Carbide Corp.) and separated by affinity chromatography on immobilized lentil lectin (Pharmacia Biotech, Inc., Piscataway, N.J.) to yield a crude brain glycoprotein fraction. This material was used to immunize C57BL/6 mice (40 µg/mouse). Lymph nodes from animals having the highest serum titers against the immunogen were fused with PcX63Ag8.653 cells (Goding, J. W. (1980) J. Immun. Meth. 39: 285–308; ATCC CRL 1580). The resulting hybridomas were screened in enzyme-linked immunosorbent assays (ELISAs) for reactivity with the immunogen and tested for reactivity in immunoblots. A hybridoma secreting an antibody designated Neuro-1 was subcloned by limiting dilution. The Neuro-1 monoclonal antibody was produced in ascites in pristane-primed Balb/C mice and purified by chromatography on Protein A-Sepharose (Sigma Chemical Co., St. Louis, Mo.).

Neuro-1, isotype IgG2b, reacts strongly with the original immunogen in enzyme-linked immunosorbent assays (ELISAs) and recognizes an approximately 135 kD polypeptide on immunoblots. Occasionally, the Neuro-1 antigen appears on immunoblots as a closely spaced doublet. The Neuro-1 producing hybridoma has been deposited with the American Type Culture Collection (Rockville, Md.) on Mar. 3, 1993 under the Accession Number HB11282 and it is the preferred monoclonal antibody for isolation and characterization of the human contactin cell adhesion molecule.

Neuro-1 monoclonal antibody was coupled to Protein A-Sepharose using methyl piperimidate (Harlow, E. and Lane, D. (1988) *Antibodies: A Laboratory Manual*, Cold Spring Harbor Press. p. 522). The membrane extracts described above were then passed over the affinity column and the bound antigen eluted using 0.1M diethylamine, pH 11.5. The eluted material was concentrated by binding to diethylaminoethyl cellulose (Whatman DE52, Fisher Scientific, Pittsburgh, Pa.) in 0.01M Tris-HCl and eluted with 1M NaCl. It was found that if frozen membrane extracts were used in the isolation procedure the Neuro-1 antigen tended to become insoluble. In these cases, the precipitated material was solubilized in deoxycholate, dialyzed against NP40-containing column buffer and processed as above.

Polyclonal antibodies were generated by immunizing animals with the material bound and eluted from immobilized Neuro-1 affinity columns. The polyclonal antibodies were further enriched by chromatography on an immobilized Neuro-1 antigen affinity column.

The 135 kD Neuro-1 antigen was characterized by binding to lentil lectin-Sepharose and elution with glucose, indicating that the polypeptide is glycosylated. The presence of asparagine-linked carbohydrate was verified by treating the antigen with endoglycosidase F (Genzyme, Cambridge, Mass.) and showing a shift to a lower molecular weight. The antigen was found to be released from the cell surface by phosphatidylinositol-specific phospholipase C, indicating that the molecule is anchored to the surface by a lipid linkage. These analyses were performed by washing crude human brain synaptosomal membrane preparations and suspending them in 0.02M NaOAc, pH 6.0. The enzyme was added and the samples were incubated for 4 hours at 37° C. The membranes were collected by centrifugation and equivalent amounts of membranes and supernatants were analyzed by immunoblotting. Treatment of the reaction mixtures with zinc or with o-phenanthrolene showed inhibition and no inhibition of release, respectively. Both polypeptides of the doublet seen on immunoblots were released by phospholipase C treatment, so it is believed that they do not represent anchored and endogenously released forms of the human contactin molecule.

The amino terminal sequence and the sequence of an internal peptide of the Neuro-1 antigen were determined and compared to the published amino acid sequences of mouse F3 and chicken contactin/F11. Amino terminal sequences were determined using immunoaffinity purified material blotted to IMMOBILON-P (Pall Corp., Glen Cove, N.Y.). The amino terminal sequence data were difficult to interpret and contained a large number of unassigned residues. Although many of these ambiguities involved amino acids which are sometimes difficult to detect by sequence analysis, it is also possible that proteolysis of the molecule creates heterogeneity at the amino terminus. Internal peptides were generated by cleavage with endopeptidase lys-c, separated by HPLC and sequenced. The sequence of the internal peptide was clear and was found to be very similar to peptides in F3 and contactin/F11. In addition, because the human peptide was generated by endopeptidase lys-c cleavage, it is most likely flanked by lysine residues. These residues are also conserved in mouse and chicken. On the basis of the amino acid sequence similarities, it is believed that the Neuro-1 antigen is the human counterpart of F3 and contactin/F11. It is therefore referred to herein as human contactin.

cDNAs encoding the Neuro-1 antigen were cloned to confirm its identity as human contactin. Mouse F3 probes were used to screen a human neuroblastoma cDNA library (Clontech, Palo Alto, Calif.). The probes were generated by reverse transcriptase-polymerase chain reaction (RT-PCR) of mouse brain polyA+ RNA using primer pairs based on the mouse F3 sequence as reported by Gennarini, et al. supra (GENBANK locus: musF3, accession #X14943). To perform the RT-PCR, mouse brain polyA+ PNA was prepared using the oligo d(T) cellulose method (Maniatis, et al. *Molecular Cloning—A Laboratory Manual*, Cold Spring Harbor Laboratory. 1982). The RT-PCR amplification reaction was based on the one-step protocol described by Goblet, et al. (1989. Nucleic Acids Res. 17: 2144). PolyA+ RNA (1 μg) and 300 ng of each primer (see below) in 66 μl DEPC water were incubated at 65° C. for 15 min. and cooled on ice. Thirty-three μl of 3× RT-PCR reagent mix (3× PCR buffer, 150 mM KCl, 30 mM Tris-Cl pH 8.3, 4.5 mM MgCl₂, 0.3% gelatin, 500 μM dNTPs, 200 U M-MLV reverse transcriptase, 4 U rRNAsin (Promega, Madison, Wis.), 2.5 U AMPLITAQ (Perlin-Elmer Cetus, Norwalk, Conn.) was added and the reaction was incubated at 37° C. for 30 min., followed by 94° C. for 1 min, 50° C. for 2 min., and 72° C. for 2 min. The amplification reaction was repeated for 40 cycles. Primer pairs A/B and C/D were used for amplification of the mouse F3 probes:

| PRIMER FIG. 1 | SEQUENCE ID NO. | SEQUENCE* | NUCLEOTIDE POSITION IN musF3 |
| --- | --- | --- | --- |
| A | SEQ ID NO:3 | CTCTGGTGATCACAAATC | 1742–1759 |
| B | SEQ ID NO:4 | TCATCTGAGAGAATCGTC | 2181–2198 |
| C | SEQ ID NO:1 | TAGACCGGATGGCCAACA | 3087–3104 |
| D | SEQ ID NO:2 | CTCGACAACATACTCTCC | 3163–3180 |

*Primers B and D are inverse complements of musF3.

The probes were verified as mouse F3 by direct sequencing with SEQUENASE (United States Biochemical Corp., Cleveland, Ohio) performed as described by Mihovilovic ((1989) BioTechniques 7: 14–16). This is an efficient method for sequencing PCR amplified DNA. The PCR products of primer pair SEQ ID NO:1/SEQ ID NO:2 (94 bp) and SEQ ID NO:3/SEQ ID NO:4 (457 bp) were gel purified and re-amplified using asymmetric primer concentrations to produce the single-stranded sequencing templates.

Using the mouse SEQ ID NO:1/SEQ ID NO:2 probe prepared above, a human Kelly neuroblastoma lambda gt10 cDNA library (Clontech, Palo Alto, Calif.) was screened as recommended by the manufacturer. Two cDNA clones were isolated, including the clone NX-7 which contained the cDNA shown in FIG. 1. To obtain clones containing upstream sequences, the neuroblastoma library was screened using the mouse SEQ ID NO:3/SEQ ID NO:4 probe. Three clones were identified from this screening, including one which was a full-length clone containing the entire coding sequence. This clone was designated clone NXII-7. Lambda cDNA inserts were either PCR amplified using lambda gt10 EcoRI forward and reverse primers and sequenced directly or subcloned into pBLUESCRIPT (SK+) (Stratagene, La Jolla, Calif.) prior to sequencing. The pBLUESCRIPT subclones were sequenced manually by either dideoxy termination with SEQUENASE or by dye-termination or dye-labeled primer automated sequencing (Applied Biosystems, Model 373A, Foster City, Calif.) as recommended by the manufacturers. Sequencing primers were synthesized on an Applied Biosystems (ABI) Model 380B DNA synthesizer and purified using OPC cartridges (ABI) as recommended. Sequence alignments, translations, and features location were performed using IG-Suite software (Intelligenetics, Mountain View, Calif.). The cDNAs produced by this procedure may be used as probes to isolate the genomic DNA coding for human contactin.

The entire human contactin cDNA coding and partial 5' and 3' untranslated sequence was determined by sequencing both strands of cDNAs (SEQ ID NO:5; EMBL Accession #Z21488). Among the various cDNA clones, two single base variations were observed at positions 2424 and 2513. These result in valine to alanine and leucine to valine transitions, respectively. Human contactin cDNA contains a 3054 bp open reading frame which is capable of encoding a polypeptide 1018 amino acids in length (SEQ ID NO:6). The predicted polypeptide contains hydrophobic segments at the amino-terminal and carboxyl-terminal ends. The amino terminal hydrophobic segment contains a consensus processing site and is believed to be a signal sequence which is cleaved to yield the amino terminus of the mature polypeptide. The hydrophobic segment at the carboxyl terminus is similar to segments found at the carboxyl ends of other phosphatidylinositol-linked membrane proteins and it is believed to be removed during the attachment to glycolipid. The fact that the Neuro-1 antigen is released from the cell surface by phosphatidylinositol-specific phospholipase C is consistent with this hypothesis. Included in the predicted amino acid sequence of the polypeptide, at positions 836–850, is the sequence of the Neuro-1 antigen lys-c peptide described above, confirming that the Neuro-1 antigen is the human contactin cell adhesion molecule.

As previously disclosed, Berglund, et al. have reported a molecule designated Gp135 which they describe as a possible human homologue of mouse F3 and chicken contactin/F11. However, the Berglund, et al. internal peptide sequence is only 71% similar to the deduced amino acid sequence of a corresponding peptide (residues 679–693) of the present invention.

The deduced amino acid sequence of human contactin contains six immunoglobulin-like domains followed by four fibronectin Type III-like repeats. This structure is similar to mouse F3 and chicken contactin/F11. In the second fibronectin Type III repeat the carboxyl-terminal conserved tyrosine is replaced by phenylalanine as in mouse F3. There are nine consensus sites for asparagine-linked glycosylation, all of which are conserved between human and mouse. The deduced human and mouse polypeptide sequences are 95% homologous and differ in size by two amino acids. Mouse F3 contains a single dipeptide insert within the sixth immunoglobulin-like domain which is absent in human contactin and chicken contactin/F11. It is not known whether this sequence gap is the result of alternate RNA splicing or a reflection of intra-exonic differences between species. The regions of lowest sequence identity have about 70% homology and are located in the hydrophobic amino terminal and carboxyl-terminal segments.

Polyclonal antisera were generated in rabbits using immunoaffinity purified human contactin to further confirm that the Neuro-1 antigen is the human homologue of F3 and contactin/F11. The sera recognized the immunogen in immunoblots at a 1:12,000 dilution. The sera also reacted with a glutathione S-transferase/human contactin fusion protein expressed in bacteria. The human contactin portion of this fusion protein comprised the carboxy-terminal region of human contactin, corresponding to the cDNA in clone NX-7, cloned in pGEX-2T (Pharmacia, Piscataway, N.J.).

The upstream EcoRI fragment of the cDNA insert of NXII-7 and the entire cDNA insert of NX-7 were used as probes to characterize the expression pattern of human contactin in various tissues. Human brain contained a single major approximately 6.5 kb MRNA. This transcript is larger than is necessary to encode the human contactin protein and is believed to include a large 3' untranslated region which is not completely represented in the cDNA clones isolated. The isolated cDNAs extended no more than about 1.2 kb past the carboxyl-terminus of the human contactin molecule.

Of the other tissues tested, pancreas and lung exhibited a low level of expression (compared to brain) of the 6.8 kb transcript and a 6.0 kb doublet similar to the pattern seen in cell lines (see below). Skeletal muscle and kidney showed similar, yet very weak 6.8 and 6.0 kb transcripts. Heart and liver were negative for human contactin transcripts. The human neuroblastoma cell lines IMR-32, SK-N-MC, SMS-KAN and SK-N-SH contained human contactin mRNA, as did the retinoblastoma cell line Y79. In these cell lines, in contrast to the transcript pattern in brain, multiple RNA species were observed—a 6.8 kb species, a 6.0 kb doublet and a 4.2 kb species. It is unclear in all cases whether or not the approximately 6.8 kb and 6.5 kb transcripts are significantly different. Rhabdomyosarcoma (A204, RD and A673), hematopoietic (KG1a.5), small cell lung carcinoma (SHP77) and Ewing Sarcoma (RD-ES) cell lines did not express human contactin RNA.

The antibodies which recognize human contactin and the nucleotide probes derived from the nucleotide sequence which codes for human contactin are useful in methods for detecting the protein and nucleotide sequences, respectively. Nucleotide probes may comprise the complete cloned cDNA sequence or a portion thereof. One skilled in the art will further recognize that nucleotide probes may be designed which comprise all or a portion of a sequence which is complementary to the cloned sequences. To detect the contactin protein, immunoassay methods involving binding between a protein and its antibody such as ELISAs and immunoblots can be readily adapted to employ the antibodies and contactin glycoprotein disclosed herein. These immunoassay methods are known in the art. In general, detection of binding between protein and antibody is accomplished by including a signal moiety in the binding reaction. This is usually in the form of a detectable label conjugated to the antibody or protein. The detectable label may be directly detectable (e.g., a dye, radioisotope or fluorochrome) or rendered detectable after further chemical reaction (e.g., an enzyme which reacts to produce a colored product or biotin which may be bound to labeled avidin).

Detection of nucleic acids by hybridization to a probe is also known in the art. Such methods as Southern blotting, dot blotting and the like may be readily adapted to detection of oligonucleotides containing all or part of a nucleic acid sequence encoding human contactin using the nucleotide sequence information of SEQ ID NO:5 to design appropriate probes. For purposes of the present invention, the terms "encoding" and "coding for" are intended to include nucleic acids which comprise sequences which can be transcribed and/or translated to produce human contactin. That is, both DNA and the RNA transcribed from it are considered to "code for" or "encode" human contactin. It will also be understood that probes derived from the disclosed nucleotide sequences may also be used to detect fragments of the disclosed coding sequences. As for immunoassays, hybridization of the probe to the contactin nucleotide sequence will be detected by means of a directly or indirectly detectable label associated with the probe, i.e., incorporated in the probe or conjugated to it. In general the same labels useful for labeling antibodies and antigens may be used to label oligonucleotides. In addition, it is within the ordinary skill in the art, given the nucleotide sequence of SEQ ID NO:5, to derive the complementary nucleotide sequence, which may also be used to prepare probes and which may be detected by hybridization to probes. Further, the present disclosure of SEQ ID NO:5 as a DNA sequence easily allows derivation of RNA sequences which are complementary to either SEQ ID NO:5 or its complementary strand. Such equivalent RNA sequences may be detected by hybridization to probes as well.

The reagents for performing these immunoassays and hybridization assays may be conveniently packaged together for sale or use in the form of a kit. A kit for immunoassay may contain an antibody which recognizes and binds to human contactin conjugated to a selected label and optionally any reagents necessary for performing the assay and detecting the label. A kit for a hybridization assay may contain short oligonucleotide probes which hybridize to one or more nucleotide sequences contained in SEQ ID NO:5, the probes being conjugated to the selected label. Optionally, the hybridization assay kit may contain any reagents necessary for performing the hybridization assay and detecting the label.

The foregoing disclosure is intended to illustrate the invention but is not to be construed as limiting its scope as defined by the appended claims. Upon reading the present disclosure, certain equivalents and variations will be apparent to one skilled in the art without the exercise of inventive skill and without departing from the spirit of the invention. Such equivalents and variations are intended to be included within its scope.

What is claimed is:

1. An antibody produced by hybridoma ATCC No. HB11282.

2. Hybridoma ATCC No. HB11282.

* * * * *

SEQUENCE LISTING ( 1 ) GENERAL INFORMATION:

( i i i ) NUMBER OF SEQUENCES: 6

( 2 ) INFORMATION FOR SEQ ID NO:1:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( v i ) ORIGINAL SOURCE:
        ( A ) ORGANISM: Mouse ( x i ) SEQUENCE DESCRIPTION: SEQ ID NO:1:

TAGACCGGAT GGCCAACA                                                                                              1 8

( 2 ) INFORMATION FOR SEQ ID NO:2:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: YES ( v i ) ORIGINAL SOURCE:
        ( A ) ORGANISM: Mouse ( x i ) SEQUENCE DESCRIPTION: SEQ ID NO:2:

CTCGACAACA TACTCTCC                                                                                              1 8

( 2 ) INFORMATION FOR SEQ ID NO:3:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( v i ) ORIGINAL SOURCE:
        ( A ) ORGANISM: Mouse ( x i ) SEQUENCE DESCRIPTION: SEQ ID NO:3:

CTCTGGTGAT CACAAATC                                                                                              1 8

( 2 ) INFORMATION FOR SEQ ID NO:4:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: YES ( v i ) ORIGINAL SOURCE:
        ( A ) ORGANISM: Mouse ( x i ) SEQUENCE DESCRIPTION: SEQ ID NO:4:

TCATCTGAGA GAATCGTC                                                                                              1 8

( 2 ) INFORMATION FOR SEQ ID NO:5:

( i ) SEQUENCE CHARACTERISTICS:
        ( A ) LENGTH: 3360 base pairs
        ( B ) TYPE: nucleic acid
        ( C ) STRANDEDNESS: both
        ( D ) TOPOLOGY: linear ( i i ) MOLECULE TYPE: cDNA ( i i i ) HYPOTHETICAL: NO ( i v ) ANTI-SENSE: NO ( v i ) ORIGINAL SOURCE:
  ( A ) ORGANISM: Homo sapiens ( i x ) FEATURE:
  ( A ) NAME/KEY: CDS
  ( B ) LOCATION: 122..3175

( i x ) FEATURE:
  ( A ) NAME/KEY: mat_peptide
  ( B ) LOCATION: 182..3100

( i x ) FEATURE:
  ( A ) NAME/KEY: sig_peptide
  ( B ) LOCATION: 122..181

( i x ) FEATURE:
  ( A ) NAME/KEY: 5'UTR
  ( B ) LOCATION: 10..121

( i x ) FEATURE:
  ( A ) NAME/KEY: 3'UTR
  ( B ) LOCATION: 3176..3360

( i x ) FEATURE:
  ( A ) NAME/KEY: polyA_site
  ( B ) LOCATION: 3281..3286

( i x ) FEATURE:
  ( A ) NAME/KEY: misc_feature
  ( B ) LOCATION: 1..9
  ( D ) OTHER INFORMATION: /function="EcoRI cloning linker"
    / product= "none"

( i x ) FEATURE:
  ( A ) NAME/KEY: misc_feature
  ( B ) LOCATION: 3101..3175
  ( D ) OTHER INFORMATION: /function="Attachment to glycolipid"
    / product= "COOH-signal peptide"

( x i ) SEQUENCE DESCRIPTION: SEQ ID NO:5:

```
GAATTCCGGC TGTGCCGCAC CGAGGCGAGC AGGAGCAGGG AACAGGTGTT TAAAATTATC      60

CAACTGCCAT AGAGCTAAAT TCTTTTTTGG AAAATTGAAC CGAACTTCTA CTGAATACAA     120

G ATG AAA ATG TGG TTG CTG GTC AGT CAT CTT GTG ATA ATA TCT ATT          166
  Met Lys Met Trp Leu Leu Val Ser His Leu Val Ile Ile Ser Ile
  -20              -15                  -10

ACT ACC TGT TTA GCA GAG TTT ACA TGG TAT AGA AGA TAT GGT CAT GGA        214
Thr Thr Cys Leu Ala Glu Phe Thr Trp Tyr Arg Arg Tyr Gly His Gly
 -5              1                 5                  10

GTT TCT GAG GAA GAC AAA GGA TTT GGA CCA ATT TTT GAA GAG CAG CCA        262
Val Ser Glu Glu Asp Lys Gly Phe Gly Pro Ile Phe Glu Glu Gln Pro
                 15                 20                 25

ATC AAT ACC ATT TAT CCA GAG GAA TCA CTG GAA GGA AAA GTC TCA CTC        310
Ile Asn Thr Ile Tyr Pro Glu Glu Ser Leu Glu Gly Lys Val Ser Leu
          30                 35                 40

AAC TGT AGG GCA CGA GCC AGC CCT TTC CCG GTT TAC AAA TGG AGA ATG        358
Asn Cys Arg Ala Arg Ala Ser Pro Phe Pro Val Tyr Lys Trp Arg Met
     45                 50                 55

AAT AAT GGG GAC GTT GAT CTC ACA AGT GAT CGA TAC AGT ATG GTA GGA        406
Asn Asn Gly Asp Val Asp Leu Thr Ser Asp Arg Tyr Ser Met Val Gly
60                 65                 70                 75

GGA AAC CTT GTT ATC AAC AAC CCT GAC AAA CAG AAA GAT GCT GGA ATA        454
Gly Asn Leu Val Ile Asn Asn Pro Asp Lys Gln Lys Asp Ala Gly Ile
              80                 85                 90
```

| | | | | | | | | | | | | | | | | |
|---|---|---|---|---|---|---|---|---|---|---|---|---|---|---|---|---|
| TAC | TAC | TGT | TTA | GCA | TCT | AAT | AAC | TAC | GGG | ATG | GTC | AGA | AGC | ACT | GAA | 502 |
| Tyr | Tyr | Cys | Leu | Ala | Ser | Asn | Asn | Tyr | Gly | Met | Val | Arg | Ser | Thr | Glu | |
| | | | 95 | | | | 100 | | | | | | 105 | | | |
| GCA | ACC | CTG | AGC | TTT | GGA | TAT | CTT | GAT | CCT | TTC | CCA | CCT | GAG | GAA | CGT | 550 |
| Ala | Thr | Leu | Ser | Phe | Gly | Tyr | Leu | Asp | Pro | Phe | Pro | Pro | Glu | Glu | Arg | |
| | | 110 | | | | | 115 | | | | | 120 | | | | |
| CCT | GAG | GTC | AGA | GTA | AAA | GAA | GGG | AAA | GGA | ATG | GTG | CTT | CTC | TGT | GAC | 598 |
| Pro | Glu | Val | Arg | Val | Lys | Glu | Gly | Lys | Gly | Met | Val | Leu | Leu | Cys | Asp | |
| | 125 | | | | | 130 | | | | | 135 | | | | | |
| CCC | CCA | TAC | CAT | TTT | CCA | GAT | GAT | CTT | AGC | TAT | CGC | TGG | CTT | CTA | AAT | 646 |
| Pro | Pro | Tyr | His | Phe | Pro | Asp | Asp | Leu | Ser | Tyr | Arg | Trp | Leu | Leu | Asn | |
| 140 | | | | | 145 | | | | | 150 | | | | | 155 | |
| GAA | TTT | CCT | GTA | TTT | ATC | ACA | ATG | GAT | AAA | CGG | CGA | TTT | GTG | TCT | CAG | 694 |
| Glu | Phe | Pro | Val | Phe | Ile | Thr | Met | Asp | Lys | Arg | Arg | Phe | Val | Ser | Gln | |
| | | | | 160 | | | | | 165 | | | | | 170 | | |
| ACA | AAT | GGC | AAT | CTC | TAC | ATT | GCA | AAT | GTT | GAG | GCT | TCC | GAC | AAA | GGC | 742 |
| Thr | Asn | Gly | Asn | Leu | Tyr | Ile | Ala | Asn | Val | Glu | Ala | Ser | Asp | Lys | Gly | |
| | | | 175 | | | | | 180 | | | | | 185 | | | |
| AAT | TAT | TCC | TGC | TTT | GTT | TCC | AGT | CCT | TCT | ATT | ACA | AAG | AGC | GTG | TTC | 790 |
| Asn | Tyr | Ser | Cys | Phe | Val | Ser | Ser | Pro | Ser | Ile | Thr | Lys | Ser | Val | Phe | |
| | | | 190 | | | | | 195 | | | | | 200 | | | |
| AGC | AAA | TTC | ATC | CCA | CTC | ATT | CCA | ATA | CCT | GAA | CGA | ACA | ACA | AAA | CCA | 838 |
| Ser | Lys | Phe | Ile | Pro | Leu | Ile | Pro | Ile | Pro | Glu | Arg | Thr | Thr | Lys | Pro | |
| | 205 | | | | | 210 | | | | | 215 | | | | | |
| TAT | CCT | GCT | GAT | ATT | GTA | GTT | CAG | TTC | AAG | GAT | GTA | TAT | GCA | TTG | ATG | 886 |
| Tyr | Pro | Ala | Asp | Ile | Val | Val | Gln | Phe | Lys | Asp | Val | Tyr | Ala | Leu | Met | |
| 220 | | | | | 225 | | | | | 230 | | | | | 235 | |
| GGC | CAA | AAT | GTG | ACC | TTA | GAA | TGT | TTT | GCA | CTT | GGA | AAT | CCT | GTT | CCG | 934 |
| Gly | Gln | Asn | Val | Thr | Leu | Glu | Cys | Phe | Ala | Leu | Gly | Asn | Pro | Val | Pro | |
| | | | | 240 | | | | | 245 | | | | | 250 | | |
| GAT | ATC | CGA | TGG | CGG | AAG | GTT | CTA | GAA | CCA | ATG | CCA | AGC | ACT | GCT | GAG | 982 |
| Asp | Ile | Arg | Trp | Arg | Lys | Val | Leu | Glu | Pro | Met | Pro | Ser | Thr | Ala | Glu | |
| | | | 255 | | | | | 260 | | | | | 265 | | | |
| ATT | AGC | ACC | TCT | GGG | GCT | GTT | CTT | AAG | ATC | TTC | AAT | ATT | CAG | CTA | GAA | 1030 |
| Ile | Ser | Thr | Ser | Gly | Ala | Val | Leu | Lys | Ile | Phe | Asn | Ile | Gln | Leu | Glu | |
| | | 270 | | | | | 275 | | | | | 280 | | | | |
| GAT | GAA | GGC | ATC | TAT | GAA | TGT | GAG | GCT | GAG | AAC | ATT | AGA | GGA | AAG | GAT | 1078 |
| Asp | Glu | Gly | Ile | Tyr | Glu | Cys | Glu | Ala | Glu | Asn | Ile | Arg | Gly | Lys | Asp | |
| | 285 | | | | | 290 | | | | | 295 | | | | | |
| AAA | CAT | CAA | GCA | AGA | ATT | TAT | GTT | CAA | GCA | TTC | CCT | GAG | TGG | GTA | GAA | 1126 |
| Lys | His | Gln | Ala | Arg | Ile | Tyr | Val | Gln | Ala | Phe | Pro | Glu | Trp | Val | Glu | |
| 300 | | | | | 305 | | | | | 310 | | | | | 315 | |
| CAC | ATC | AAT | GAC | ACA | GAG | GTG | GAC | ATA | GGC | AGT | GAT | CTC | TAC | TGG | CCT | 1174 |
| His | Ile | Asn | Asp | Thr | Glu | Val | Asp | Ile | Gly | Ser | Asp | Leu | Tyr | Trp | Pro | |
| | | | | 320 | | | | | 325 | | | | | 330 | | |
| TGT | GTG | GCC | ACA | GGA | AAG | CCC | ATC | CCT | ACA | ATC | CGA | TGG | TTG | AAA | AAT | 1222 |
| Cys | Val | Ala | Thr | Gly | Lys | Pro | Ile | Pro | Thr | Ile | Arg | Trp | Leu | Lys | Asn | |
| | | | 335 | | | | | 340 | | | | | 345 | | | |
| GGA | TAT | GCG | TAT | CAT | AAA | GGG | GAA | TTA | AGA | CTG | TAT | GAT | GTG | ACT | TTT | 1270 |
| Gly | Tyr | Ala | Tyr | His | Lys | Gly | Glu | Leu | Arg | Leu | Tyr | Asp | Val | Thr | Phe | |
| | | 350 | | | | | 355 | | | | | 360 | | | | |
| GAA | AAT | GCC | GGA | ATG | TAT | CAG | TGC | ATA | GCT | GAA | AAC | ACA | TAT | GGA | GCC | 1318 |
| Glu | Asn | Ala | Gly | Met | Tyr | Gln | Cys | Ile | Ala | Glu | Asn | Thr | Tyr | Gly | Ala | |
| | 365 | | | | | 370 | | | | | 375 | | | | | |
| ATT | TAT | GCA | AAT | GCT | GAG | TTG | AAG | ATC | TTG | GCG | TTG | GCT | CCA | ACT | TTT | 1366 |
| Ile | Tyr | Ala | Asn | Ala | Glu | Leu | Lys | Ile | Leu | Ala | Leu | Ala | Pro | Thr | Phe | |
| 380 | | | | | 385 | | | | | 390 | | | | | 395 | |
| GAA | ATG | AAT | CCT | ATG | AAG | AAA | AAG | ATC | CTG | GCT | GCT | AAA | GGT | GGA | AGG | 1414 |
| Glu | Met | Asn | Pro | Met | Lys | Lys | Lys | Ile | Leu | Ala | Ala | Lys | Gly | Gly | Arg | |
| | | | | 400 | | | | | 405 | | | | | 410 | | |

-continued

| | | | | | | | | | | | | | | | | |
|---|---|---|---|---|---|---|---|---|---|---|---|---|---|---|---|---|
| GTG | ATA | ATT | GAA | TGC | AAA | CCT | AAA | GCT | GCA | CCG | AAA | CCA | AAG | TTT | TCA | 1462 |
| Val | Ile | Ile | Glu 415 | Cys | Lys | Pro | Lys 420 | Ala | Ala | Pro | Lys | Pro 425 | Lys | Phe | Ser | |
| TGG | AGT | AAA | GGG | ACA | GAG | TGG | CTT | GTC | AAT | AGC | AGC | AGA | ATA | CTC | ATT | 1510 |
| Trp | Ser | Lys 430 | Gly | Thr | Glu | Trp | Leu 435 | Val | Asn | Ser | Ser 440 | Arg | Ile | Leu | Ile | |
| TGG | GAA | GAT | GGT | AGC | TTG | GAA | ATC | AAC | AAC | ATT | ACA | AGG | AAT | GAT | GGA | 1558 |
| Trp | Glu 445 | Asp | Gly | Ser | Leu | Glu 450 | Ile | Asn | Asn | Ile | Thr 455 | Arg | Asn | Asp | Gly | |
| GGT | ATC | TAT | ACA | TGC | TTT | GCA | GAA | AAT | AAC | AGA | GGG | AAA | GCT | AAT | AGC | 1606 |
| Gly 460 | Ile | Tyr | Thr | Cys | Phe 465 | Ala | Glu | Asn | Asn | Arg 470 | Gly | Lys | Ala | Asn | Ser 475 | |
| ACT | GGA | ACC | CTT | GTT | ATC | ACA | GAT | CCT | ACG | CGA | ATT | ATA | TTG | GCC | CCA | 1654 |
| Thr | Gly | Thr | Leu | Val 480 | Ile | Thr | Asp | Pro | Thr 485 | Arg | Ile | Ile | Leu | Ala 490 | Pro | |
| ATT | AAT | GCC | GAT | ATC | ACA | GTT | GGA | GAA | AAC | GCC | ACC | ATG | CAG | TGT | GCT | 1702 |
| Ile | Asn | Ala | Asp 495 | Ile | Thr | Val | Gly | Glu 500 | Asn | Ala | Thr | Met | Gln 505 | Cys | Ala | |
| GCG | TCC | TTT | GAT | CCT | GCC | TTG | GAT | CTC | ACA | TTT | GTT | TGG | TCC | TTC | AAT | 1750 |
| Ala | Ser | Phe 510 | Asp | Pro | Ala | Leu | Asp 515 | Leu | Thr | Phe | Val | Trp 520 | Ser | Phe | Asn | |
| GGC | TAT | GTG | ATC | GAT | TTT | AAC | AAA | GAG | AAT | ATT | CAC | TAC | CAG | AGG | AAT | 1798 |
| Gly | Tyr 525 | Val | Ile | Asp | Phe | Asn 530 | Lys | Glu | Asn | Ile | His 535 | Tyr | Gln | Arg | Asn | |
| TTT | ATG | CTG | GAT | TCC | AAT | GGG | GAA | TTA | CTA | ATC | CGA | AAT | GCG | CAG | CTG | 1846 |
| Phe 540 | Met | Leu | Asp | Ser | Asn 545 | Gly | Glu | Leu | Leu | Ile 550 | Arg | Asn | Ala | Gln | Leu 555 | |
| AAA | CAT | GCT | GGA | AGA | TAC | ACA | TGC | ACT | GCC | CAG | ACA | ATT | GTG | GAC | AAT | 1894 |
| Lys | His | Ala | Gly | Arg 560 | Tyr | Thr | Cys | Thr | Ala 565 | Gln | Thr | Ile | Val | Asp 570 | Asn | |
| TCT | TCA | GCT | TCA | GCT | GAC | CTT | GTA | GTG | AGA | GGC | CCT | CCA | GGC | CCT | CCA | 1942 |
| Ser | Ser | Ala | Ser 575 | Ala | Asp | Leu | Val | Val 580 | Arg | Gly | Pro | Pro | Gly 585 | Pro | Pro | |
| GGT | GGT | CTG | AGA | ATA | GAA | GAC | ATT | AGA | GCC | ACT | TCT | GTG | GCA | CTT | ACT | 1990 |
| Gly | Gly | Leu | Arg 590 | Ile | Glu | Asp | Ile | Arg 595 | Ala | Thr | Ser | Val | Ala 600 | Leu | Thr | |
| TGG | AGC | CGT | GGT | TCA | GAC | AAT | CAT | AGT | CCT | ATT | TCT | AAA | TAC | ACT | ATC | 2038 |
| Trp | Ser | Arg 605 | Gly | Ser | Asp | Asn | His 610 | Ser | Pro | Ile | Ser | Lys 615 | Tyr | Thr | Ile | |
| CAG | ACC | AAG | ACT | ATT | CTT | TCA | GAT | GAC | TGG | AAA | GAT | GCA | AAG | ACA | GAT | 2086 |
| Gln 620 | Thr | Lys | Thr | Ile | Leu 625 | Ser | Asp | Asp | Trp | Lys 630 | Asp | Ala | Lys | Thr | Asp 635 | |
| CCC | CCA | ATT | ATT | GAA | GGA | AAT | ATG | GAG | GCA | GCA | AGA | GCA | GTG | GAC | TTA | 2134 |
| Pro | Pro | Ile | Ile | Glu 640 | Gly | Asn | Met | Glu | Ala 645 | Ala | Arg | Ala | Val | Asp 650 | Leu | |
| ATC | CCA | TGG | ATG | GAG | TAT | GAA | TTC | CGC | GTG | GTA | GCA | ACC | AAT | ACA | CTG | 2182 |
| Ile | Pro | Trp | Met 655 | Glu | Tyr | Glu | Phe | Arg 660 | Val | Val | Ala | Thr | Asn 665 | Thr | Leu | |
| GGT | AGA | GGA | GAG | CCC | AGT | ATA | CCA | TCT | AAC | AGA | ATT | AAA | ACA | GAC | GGT | 2230 |
| Gly | Arg | Gly 670 | Glu | Pro | Ser | Ile | Pro 675 | Ser | Asn | Arg | Ile | Lys 680 | Thr | Asp | Gly | |
| GCT | GCA | CCA | AAT | GTG | GCT | CCT | TCA | GAT | GTA | GGA | GGT | GGA | GGT | GGA | AGA | 2278 |
| Ala | Ala | Pro 685 | Asn | Val | Ala | Pro | Ser 690 | Asp | Val | Gly | Gly | Gly 695 | Gly | Gly | Arg | |
| AAC | AGA | GAG | CTG | ACC | ATA | ACA | TGG | GCG | CCT | TTG | TCA | AGA | GAA | TAC | CAC | 2326 |
| Asn | Arg | Glu | Leu | Thr | Ile | Thr 705 | Trp | Ala | Pro | Leu | Ser 710 | Arg | Glu | Tyr | His 715 | |
| Asn 700 | | | | | | | | | | | | | | | | |
| TAT | GGC | AAC | AAT | TTT | GGT | TAC | ATA | GTG | GCA | TTT | AAG | CCA | TTT | GAT | GGA | 2374 |
| Tyr | Gly | Asn | Asn | Phe 720 | Gly | Tyr | Ile | Val | Ala 725 | Phe | Lys | Pro | Phe | Asp 730 | Gly | |

-continued

| | | | | | | | | | | | | | | | |
|---|---|---|---|---|---|---|---|---|---|---|---|---|---|---|---|
| GAA | GAA | TGG | AAA | AAA | GTC | ACA | GTT | ACT | AAT | CCT | GAT | ACT | GGC | CGA | TAT | 2422 |
| Glu | Glu | Trp | Lys | Lys | Val | Thr | Val | Thr | Asn | Pro | Asp | Thr | Gly | Arg | Tyr |
| | | | 735 | | | | 740 | | | | | 745 | | | |
| GTC | CAT | AAA | GAT | GAA | ACC | ATG | AGC | CCT | TCC | ACT | GCA | TTT | CAA | GTT | AAA | 2470 |
| Val | His | Lys | Asp | Glu | Thr | Met | Ser | Pro | Ser | Thr | Ala | Phe | Gln | Val | Lys |
| | | 750 | | | | | 755 | | | | | 760 | | | |
| GTC | AAG | GCC | TTC | AAC | AAC | AAA | GGA | GAT | GGA | CCT | TAC | AGC | CTA | CTA | GCA | 2518 |
| Val | Lys | Ala | Phe | Asn | Asn | Lys | Gly | Asp | Gly | Pro | Tyr | Ser | Leu | Leu | Ala |
| | 765 | | | | | 770 | | | | | 775 | | | | |
| GTC | ATT | AAT | TCA | GCA | CAA | GAC | GCT | CCC | AGT | GAA | GCC | CCA | ACA | GAA | GTA | 2566 |
| Val | Ile | Asn | Ser | Ala | Gln | Asp | Ala | Pro | Ser | Glu | Ala | Pro | Thr | Glu | Val |
| 780 | | | | | 785 | | | | | 790 | | | | | 795 |
| GGT | GTA | AAA | GTC | TTA | TCA | TCT | TCT | GAG | ATA | TCT | GTT | CAT | TGG | GAA | CAT | 2614 |
| Gly | Val | Lys | Val | Leu | Ser | Ser | Ser | Glu | Ile | Ser | Val | His | Trp | Glu | His |
| | | | | 800 | | | | | 805 | | | | | 810 | |
| GTT | TTA | GAA | AAA | ATA | GTG | GAA | AGC | TAT | CAG | ATT | CGG | TAT | TGG | GCT | GCC | 2662 |
| Val | Leu | Glu | Lys | Ile | Val | Glu | Ser | Tyr | Gln | Ile | Arg | Tyr | Trp | Ala | Ala |
| | | | 815 | | | | | 820 | | | | | 825 | | |
| CAT | GAC | AAA | GAA | GAA | GCT | GCA | AAC | AGA | GTT | CAA | GTC | ACC | AGC | CAA | GAG | 2710 |
| His | Asp | Lys | Glu | Glu | Ala | Ala | Asn | Arg | Val | Gln | Val | Thr | Ser | Gln | Glu |
| | | 830 | | | | | 835 | | | | | 840 | | | |
| TAC | TCG | GCC | AGG | CTC | GAG | AAC | CTT | CTG | CCA | GAC | ACC | CAG | TAT | TTT | ATA | 2758 |
| Tyr | Ser | Ala | Arg | Leu | Glu | Asn | Leu | Leu | Pro | Asp | Thr | Gln | Tyr | Phe | Ile |
| | 845 | | | | | 850 | | | | | 855 | | | | |
| GAA | GTC | GGG | GCC | TGC | AAT | AGT | GCA | GGG | TGT | GGA | CCT | CCA | AGT | GAC | ATG | 2806 |
| Glu | Val | Gly | Ala | Cys | Asn | Ser | Ala | Gly | Cys | Gly | Pro | Pro | Ser | Asp | Met |
| 860 | | | | | 865 | | | | | 870 | | | | | 875 |
| ATT | GAG | GCT | TTC | ACC | AAG | AAA | GCA | CCT | CCT | AGC | CAG | CCT | CCA | AGG | ATC | 2854 |
| Ile | Glu | Ala | Phe | Thr | Lys | Lys | Ala | Pro | Pro | Ser | Gln | Pro | Pro | Arg | Ile |
| | | | | 880 | | | | | 885 | | | | | 890 | |
| ATC | AGT | TCA | GTA | AGG | TCT | GGT | TCA | CGC | TAT | ATA | ATC | ACC | TGG | GAT | CAT | 2902 |
| Ile | Ser | Ser | Val | Arg | Ser | Gly | Ser | Arg | Tyr | Ile | Ile | Thr | Trp | Asp | His |
| | | | 895 | | | | | 900 | | | | | 905 | | |
| GTC | GTT | GCA | CTA | TCA | AAT | GAA | TCT | ACA | GTG | ACG | GGA | TAT | AAG | GTA | CTC | 2950 |
| Val | Val | Ala | Leu | Ser | Asn | Glu | Ser | Thr | Val | Thr | Gly | Tyr | Lys | Val | Leu |
| | | 910 | | | | | 915 | | | | | 920 | | | |
| TAC | AGA | CCT | GAT | GGC | CAG | CAT | GAT | GGC | AAG | CTG | TAT | TCA | ACT | CAC | AAA | 2998 |
| Tyr | Arg | Pro | Asp | Gly | Gln | His | Asp | Gly | Lys | Leu | Tyr | Ser | Thr | His | Lys |
| | 925 | | | | | 930 | | | | | 935 | | | | |
| CAC | TCC | ATA | GAA | GTC | CCA | ATC | CCC | AGA | GAT | GGA | GAA | TAC | GTT | GTG | GAG | 3046 |
| His | Ser | Ile | Glu | Val | Pro | Ile | Pro | Arg | Asp | Gly | Glu | Tyr | Val | Val | Glu |
| 940 | | | | | 945 | | | | | 950 | | | | | 955 |
| GTT | CGC | GCG | CAC | AGT | GAT | GGA | GGA | GAT | GGA | GTG | GTG | TCT | CAA | GTC | AAA | 3094 |
| Val | Arg | Ala | His | Ser | Asp | Gly | Gly | Asp | Gly | Val | Val | Ser | Gln | Val | Lys |
| | | | | 960 | | | | | 965 | | | | | 970 | |
| ATT | TCA | GGT | GCA | CCC | ACC | CTA | TCC | CCA | AGT | CTT | CTC | GGC | TTA | CTG | CTG | 3142 |
| Ile | Ser | Gly | Ala | Pro | Thr | Leu | Ser | Pro | Ser | Leu | Leu | Gly | Leu | Leu | Leu |
| | | | 975 | | | | | 980 | | | | | 985 | | |
| CCT | GCC | TTT | GGC | ATC | CTT | GTC | TAC | TTG | GAA | TTC | TGAATGTGTT | | GTGACAGCTG | | | 3195 |
| Pro | Ala | Phe | Gly | Ile | Leu | Val | Tyr | Leu | Glu | Phe |
| | | 990 | | | | | 995 | | | |

CTGTTCCCAT CCCAGCTCAG AAGACACCCT TCAACCCTGG GATGACCACA ATTCCTTCCA    3255

ATTTCTGCGG CTCCATCCTA AGCCAAATAA ATTATACTTT AACAAACTAT TCAACTGATT    3315

TACAACACAC ATGATGACTG AGGCATTCAG GAACCCCTTC ATCCA    3360

( 2 ) INFORMATION FOR SEQ ID NO:6:

( i ) SEQUENCE CHARACTERISTICS:
        ( A ) LENGTH: 1018 amino acids
        ( B ) TYPE: amino acid (D) TOPOLOGY: linear (ii) MOLECULE TYPE: protein (vi) ORIGINAL SOURCE:
    (A) ORGANISM: Homo sapiens (ix) FEATURE:
    (A) NAME/KEY: Disulfide-bond
    (B) LOCATION: 45..94

(ix) FEATURE:
    (A) NAME/KEY: Disulfide-bond
    (B) LOCATION: 138..191

(ix) FEATURE:
    (A) NAME/KEY: Disulfide-bond
    (B) LOCATION: 243..290

(ix) FEATURE:
    (A) NAME/KEY: Disulfide-bond
    (B) LOCATION: 332..371

(ix) FEATURE:
    (A) NAME/KEY: Disulfide-bond
    (B) LOCATION: 416..464

(ix) FEATURE:
    (A) NAME/KEY: Disulfide-bond
    (B) LOCATION: 506..563

(ix) FEATURE:
    (A) NAME/KEY: Domain
    (B) LOCATION: 604..657
    (D) OTHER INFORMATION: /label=FLR
        / note= "conserved core of fibronectin type
        III-like repeat"

(ix) FEATURE:
    (A) NAME/KEY: Domain
    (B) LOCATION: 707..760
    (D) OTHER INFORMATION: /label=FLR
        / note= "conserved core of fibronectin type
        III-like repeat"

(ix) FEATURE:
    (A) NAME/KEY: Domain
    (B) LOCATION: 809..857
    (D) OTHER INFORMATION: /label=FLR
        / note= "conserved core of fibronectin type
        III-like repeat"

(ix) FEATURE:
    (A) NAME/KEY: Domain
    (B) LOCATION: 905..952
    (D) OTHER INFORMATION: /label=FLR
        / note= "conserved core of fibronectin type
        III-like repeat"

(ix) FEATURE:
    (A) NAME/KEY: Modified-site
    (B) LOCATION: 188
    (D) OTHER INFORMATION: /label=ASN-glycos
        / note= "potential site of ASN-linked
        glycosylation"

(ix) FEATURE:
    (A) NAME/KEY: Modified-site
    (B) LOCATION: 238
    (D) OTHER INFORMATION: /label=ASN-glycos
        / note= "potential site of ASN-linked
        glycosylation"

(ix) FEATURE:
    (A) NAME/KEY: Modified-site
    (B) LOCATION: 318
    (D) OTHER INFORMATION: /label=ASN-glycos
        / note= "potential site of ASN-linked
        glycosylation"

(ix) FEATURE:
    (A) NAME/KEY: Modified-site
    (B) LOCATION: 437
    (D) OTHER INFORMATION: /label=ASN-glycos
        / note= "potential site of ASN-linked glycosylation"

(ix) FEATURE:
    (A) NAME/KEY: Modified-site
    (B) LOCATION: 453
    (D) OTHER INFORMATION: /label=ASN-glycos
        / note= "potential site of ASN-linked glycosylation"

(ix) FEATURE:
    (A) NAME/KEY: Modified-site
    (B) LOCATION: 474
    (D) OTHER INFORMATION: /label=ASN-glycos
        / note= "potential site of ASN-linked glycosylation"

(ix) FEATURE:
    (A) NAME/KEY: Modified-site
    (B) LOCATION: 501
    (D) OTHER INFORMATION: /label=ASN-glycos
        / note= "potential site of ASN-linked glycosylation"

(ix) FEATURE:
    (A) NAME/KEY: Modified-site
    (B) LOCATION: 571
    (D) OTHER INFORMATION: /label=ASN-glycos
        / note= "potential site of ASN-linked B glycosylation"

(ix) FEATURE:
    (A) NAME/KEY: Modified-site
    (B) LOCATION: 913
    (D) OTHER INFORMATION: /label=ASN-glycos
        / note= "potential site of ASN-linked glycosylation"

(xi) SEQUENCE DESCRIPTION: SEQ ID NO:6:

```
Met Lys Met Trp Leu Leu Val Ser His Leu Val Ile Ile Ser Ile Thr
-20             -15                 -10                     -5

Thr Cys Leu Ala Glu Phe Thr Trp Tyr Arg Arg Tyr Gly His Gly Val
                  1              5                     10

Ser Glu Glu Asp Lys Gly Phe Gly Pro Ile Phe Glu Glu Gln Pro Ile
         15                  20                 25

Asn Thr Ile Tyr Pro Glu Glu Ser Leu Glu Gly Lys Val Ser Leu Asn
         30                  35              40

Cys Arg Ala Arg Ala Ser Pro Phe Pro Val Tyr Lys Trp Arg Met Asn
 45                  50                  55                      60

Asn Gly Asp Val Asp Leu Thr Ser Asp Arg Tyr Ser Met Val Gly Gly
                 65                  70                      75

Asn Leu Val Ile Asn Asn Pro Asp Lys Gln Lys Asp Ala Gly Ile Tyr
             80                  85                  90

Tyr Cys Leu Ala Ser Asn Asn Tyr Gly Met Val Arg Ser Thr Glu Ala
         95                 100                 105

Thr Leu Ser Phe Gly Tyr Leu Asp Pro Phe Pro Pro Glu Glu Arg Pro
     110                 115                 120

Glu Val Arg Val Lys Glu Gly Lys Gly Met Val Leu Leu Cys Asp Pro
125                 130                 135                 140

Pro Tyr His Phe Pro Asp Asp Leu Ser Tyr Arg Trp Leu Leu Asn Glu
             145                 150                 155

Phe Pro Val Phe Ile Thr Met Asp Lys Arg Arg Phe Val Ser Gln Thr
             160                 165                 170
```

```
Asn Gly Asn Leu Tyr Ile Ala Asn Val Glu Ala Ser Asp Lys Gly Asn
        175                 180                 185
Tyr Ser Cys Phe Val Ser Ser Pro Ser Ile Thr Lys Ser Val Phe Ser
        190                 195                 200
Lys Phe Ile Pro Leu Ile Pro Ile Pro Glu Arg Thr Thr Lys Pro Tyr
205                     210                 215                 220
Pro Ala Asp Ile Val Val Gln Phe Lys Asp Val Tyr Ala Leu Met Gly
                    225                 230                 235
Gln Asn Val Thr Leu Glu Cys Phe Ala Leu Gly Asn Pro Val Pro Asp
                240                 245                 250
Ile Arg Trp Arg Lys Val Leu Glu Pro Met Pro Ser Thr Ala Glu Ile
            255                 260                 265
Ser Thr Ser Gly Ala Val Leu Lys Ile Phe Asn Ile Gln Leu Glu Asp
        270                 275                 280
Glu Gly Ile Tyr Glu Cys Glu Ala Glu Asn Ile Arg Gly Lys Asp Lys
285                     290                 295                 300
His Gln Ala Arg Ile Tyr Val Gln Ala Phe Pro Glu Trp Val Glu His
                305                 310                 315
Ile Asn Asp Thr Glu Val Asp Ile Gly Ser Asp Leu Tyr Trp Pro Cys
            320                 325                 330
Val Ala Thr Gly Lys Pro Ile Pro Thr Ile Arg Trp Leu Lys Asn Gly
        335                 340                 345
Tyr Ala Tyr His Lys Gly Glu Leu Arg Leu Tyr Asp Val Thr Phe Glu
        350                 355                 360
Asn Ala Gly Met Tyr Gln Cys Ile Ala Glu Asn Thr Tyr Gly Ala Ile
365                     370                 375                 380
Tyr Ala Asn Ala Glu Leu Lys Ile Leu Ala Leu Ala Pro Thr Phe Glu
                385                 390                 395
Met Asn Pro Met Lys Lys Lys Ile Leu Ala Ala Lys Gly Gly Arg Val
            400                 405                 410
Ile Ile Glu Cys Lys Pro Lys Ala Ala Pro Lys Pro Lys Phe Ser Trp
        415                 420                 425
Ser Lys Gly Thr Glu Trp Leu Val Asn Ser Ser Arg Ile Leu Ile Trp
        430                 435                 440
Glu Asp Gly Ser Leu Glu Ile Asn Asn Ile Thr Arg Asn Asp Gly Gly
445                     450                 455                 460
Ile Tyr Thr Cys Phe Ala Glu Asn Asn Arg Gly Lys Ala Asn Ser Thr
                465                 470                 475
Gly Thr Leu Val Ile Thr Asp Pro Thr Arg Ile Ile Leu Ala Pro Ile
            480                 485                 490
Asn Ala Asp Ile Thr Val Gly Glu Asn Ala Thr Met Gln Cys Ala Ala
        495                 500                 505
Ser Phe Asp Pro Ala Leu Asp Leu Thr Phe Val Trp Ser Phe Asn Gly
        510                 515                 520
Tyr Val Ile Asp Phe Asn Lys Glu Asn Ile His Tyr Gln Arg Asn Phe
525                     530                 535                 540
Met Leu Asp Ser Asn Gly Glu Leu Leu Ile Arg Asn Ala Gln Leu Lys
                545                 550                 555
His Ala Gly Arg Tyr Thr Cys Thr Ala Gln Thr Ile Val Asp Asn Ser
            560                 565                 570
Ser Ala Ser Ala Asp Leu Val Val Arg Gly Pro Pro Gly Pro Pro Gly
        575                 580                 585
Gly Leu Arg Ile Glu Asp Ile Arg Ala Thr Ser Val Ala Leu Thr Trp
        590                 595                 600
```

-continued

| | | | | | | | | | | | | | | |
|---|---|---|---|---|---|---|---|---|---|---|---|---|---|---|
| Ser 605 | Arg | Gly | Ser | Asp | Asn 610 | His | Ser | Pro | Ile | Ser 615 | Lys | Tyr | Thr | Ile | Gln 620 |
| Thr | Lys | Thr | Ile | Leu 625 | Ser | Asp | Asp | Trp | Lys 630 | Asp | Ala | Lys | Thr | Asp 635 | Pro |
| Pro | Ile | Ile | Glu 640 | Gly | Asn | Met | Glu | Ala 645 | Ala | Arg | Ala | Val | Asp 650 | Leu | Ile |
| Pro | Trp | Met 655 | Glu | Tyr | Glu | Phe | Arg 660 | Val | Val | Ala | Thr | Asn 665 | Thr | Leu | Gly |
| Arg | Gly 670 | Glu | Pro | Ser | Ile | Pro 675 | Ser | Asn | Arg | Ile | Lys 680 | Thr | Asp | Gly | Ala |
| Ala 685 | Pro | Asn | Val | Ala | Pro 690 | Ser | Asp | Val | Gly | Gly 695 | Gly | Gly | Gly | Arg | Asn 700 |
| Arg | Glu | Leu | Thr | Ile 705 | Thr | Trp | Ala | Pro | Leu 710 | Ser | Arg | Glu | Tyr | His 715 | Tyr |
| Gly | Asn | Asn | Phe 720 | Gly | Tyr | Ile | Val | Ala 725 | Phe | Lys | Pro | Phe | Asp 730 | Gly | Glu |
| Glu | Trp | Lys 735 | Lys | Val | Thr | Val | Thr 740 | Asn | Pro | Asp | Thr | Gly 745 | Arg | Tyr | Val |
| His | Lys 750 | Asp | Glu | Thr | Met | Ser 755 | Pro | Ser | Thr | Ala | Phe 760 | Gln | Val | Lys | Val |
| Lys 765 | Ala | Phe | Asn | Asn | Lys 770 | Gly | Asp | Gly | Pro | Tyr 775 | Ser | Leu | Leu | Ala | Val 780 |
| Ile | Asn | Ser | Ala | Gln 785 | Asp | Ala | Pro | Ser | Glu 790 | Ala | Pro | Thr | Glu | Val 795 | Gly |
| Val | Lys | Val | Leu 800 | Ser | Ser | Ser | Glu | Ile 805 | Ser | Val | His | Trp | Glu 810 | His | Val |
| Leu | Glu | Lys 815 | Ile | Val | Glu | Ser | Tyr 820 | Gln | Ile | Arg | Tyr | Trp 825 | Ala | Ala | His |
| Asp | Lys 830 | Glu | Glu | Ala | Ala | Asn 835 | Arg | Val | Gln | Val | Thr 840 | Ser | Gln | Glu | Tyr |
| Ser 845 | Ala | Arg | Leu | Glu | Asn 850 | Leu | Leu | Pro | Asp | Thr 855 | Gln | Tyr | Phe | Ile | Glu 860 |
| Val | Gly | Ala | Cys | Asn 865 | Ser | Ala | Gly | Cys | Gly 870 | Pro | Pro | Ser | Asp | Met 875 | Ile |
| Glu | Ala | Phe | Thr 880 | Lys | Lys | Ala | Pro | Pro 885 | Ser | Gln | Pro | Pro | Arg 890 | Ile | Ile |
| Ser | Ser | Val 895 | Arg | Ser | Gly | Ser | Arg 900 | Tyr | Ile | Ile | Thr | Trp 905 | Asp | His | Val |
| Val | Ala 910 | Leu | Ser | Asn | Glu | Ser 915 | Thr | Val | Thr | Gly | Tyr 920 | Lys | Val | Leu | Tyr |
| Arg 925 | Pro | Asp | Gly | Gln | His 930 | Asp | Gly | Lys | Leu | Tyr 935 | Ser | Thr | His | Lys | His 940 |
| Ser | Ile | Glu | Val | Pro 945 | Ile | Pro | Arg | Asp | Gly 950 | Glu | Tyr | Val | Val | Glu 955 | Val |
| Arg | Ala | His | Ser 960 | Asp | Gly | Gly | Asp | Gly 965 | Val | Val | Ser | Gln | Val 970 | Lys | Ile |
| Ser | Gly | Ala 975 | Pro | Thr | Leu | Ser | Pro 980 | Ser | Leu | Leu | Gly | Leu 985 | Leu | Leu | Pro |
| Ala | Phe 990 | Gly | Ile | Leu | Val | Tyr 995 | Leu | Glu | Phe | | | | | | |